United States Patent [19]

Pereira et al.

[11] Patent Number: 6,001,751

[45] Date of Patent: Dec. 14, 1999

[54] NONWOVEN FABRIC OF MULTI-LENGTH, MULTI-DENIER FIBERS AND ABSORBENT ARTICLE FORMED THEREFROM

[75] Inventors: Jose Antonio Pereira; Eduardo Cesar Andreo Aledo, both of Estado de Sao Paulo, Brazil

[73] Assignee: McNeil-PPC, Inc., Skillman, N.J.

[21] Appl. No.: 09/054,679

[22] Filed: Apr. 3, 1998

[30] Foreign Application Priority Data

Apr. 30, 1997 [BR] Brazil ..................................... 9701974

[51] Int. Cl.⁶ .............................. B32B 5/16; A61F 13/15
[52] U.S. Cl. .......................... 442/334; 442/59; 442/375; 604/385.1
[58] Field of Search .............................. 442/59, 375, 327, 442/334

[56] References Cited

U.S. PATENT DOCUMENTS

| | | | |
|---|---|---|---|
| 5,431,643 | 7/1995 | Ouellette et al. | 604/385.1 |
| 5,575,874 | 11/1996 | Griesbach, III et al. | 156/167 |
| 5,716,349 | 2/1998 | Taylor et al. | 604/385.1 |
| 5,803,920 | 9/1998 | Gilman | 604/378 |
| 5,817,394 | 10/1998 | Alikhan et al. | 428/137 |
| 5,821,179 | 10/1998 | Masaki et al. | 442/375 |

*Primary Examiner*—Terrel Morris
*Assistant Examiner*—Ula Ruddock
*Attorney, Agent, or Firm*—James P. Barr

[57] ABSTRACT

The present invention is directed to a nonwoven fabric which is formed from a network of interconnected multi-length, multi-denier thermoplastic fibers. The nonwoven fabrics of the present invention provide enhanced comfort and performance not found in conventional nonwoven fabrics and have been found to be particularly useful as cover materials in disposable sanitary absorbent articles.

15 Claims, No Drawings

NONWOVEN FABRIC OF MULTI-LENGTH, MULTI-DENIER FIBERS AND ABSORBENT ARTICLE FORMED THEREFROM

FIELD OF THE INVENTION

This invention relates to a new nonwoven fabric, the fabric being specifically suitable for use as contact surface with a user's body in disposable absorbent products, surgical bandages, female hygienic tampons, powder or cleansing fabrics, and similar items. More particularly, the present invention relates to a nonwoven fabric made from a network of interconnected staple fibers wherein the fibers include a mixture of at least two sets of staple fibers, each set having a length which is different than the other set by at least two millimeters.

BACKGROUND OF THE INVENTION

Medical and disposable absorbent products usually include a body-facing covering or lining material formed from a nonwoven fabric. Typical nonwoven fabrics are derived from fibers or filaments which are chemically, hydraulically, thermally or mechanically linked together and made through technologies which are known to the expert such as, for example, "thermobonding", "spunbonding" or "through air bonding". Such fabrics must be comfortable, capable of remaining in contact with internal and external surfaces of the body for prolonged periods without causing itching or allergic reactions and capable of transmitting body fluids to a central absorbent core. In an attempt to provide absorbent articles with covering or lining materials which remain clean and dry during their use, it is conventional to use synthetic fibers such as polypropylene, polyethylene, polyester and the like.

Nonwoven fabric coverings of synthetic fibers of up to 3 denier have been used as coverings for personal disposable absorbent articles. These fabrics, though they possess great softness due to the fine denier of their fibers, tend to retain more liquids than desired due to the small capillary pore size provided by these fine denier fibers. Alternatively, an increase in fiber denier results in a decrease in fluid retention, but the softness of the fabric is decreased. Therefore, the search for an adequate technical solution still persists.

SUMMARY OF THE INVENTION

It is an object of the present invention to provide a nonwoven fabric which is useful as covering for personal absorbent articles for surfaces which are intended to contact a user's body.

It is another object of the present invention to provide a nonwoven fabric which has a pleasant touch and marked softness and yet provides enhanced fluid absorbency capabilities.

It is another object of the present invention to provide an absorbent article which uses a nonwoven fabric covering formed from at least two sets of staple, multi-length fibers, the length of one set being different than the other set by at least two millimeters.

It is another object of the present invention to provide an absorbent article which uses a nonwoven fabric covering formed from at least two sets of staple, multi-length fibers and having fibers of more than one denier.

These and other objects of the present invention shall be better understood in the detailed description below.

In accordance with the present invention a new nonwoven fabric was created and characterized by a network of interconnected staple fibers formed by a mixture of at least two sets of staple fibers, each set of fibers having different average fiber lengths. Suitable fibers for use in this invention have a length of at least about 2 mm, and are generally in the range of from 2 mm to about 100 mm. The fibers of one set have an average fiber length which is greater than an average fiber length of a second set by at least 2 mm. As used herein, the terminology "fiber length" refers to an average length of one set of fibers. Accordingly, staple fibers having a length of 32 mm, for example, refer to a set of staple fibers having an average length of 32 mm, with a slight distribution of values around that number, usually with a normal statistic distribution. This distribution may range up to about +/–20% of the average fiber length of the staple fibers in the set.

As used herein, the terms "nonwoven" and "nonwoven fabric" are understood to be synonymous. Also as used herein, the terminology "mono-length" refers to a set of staple fibers with only one length. Also as used herein, the terminology "multi-length", refers to a blend of staple fibers having more than one measure of length. Also as used herein, the terminology "mono-denier" refers to a set of fibers or to a fabric containing fibers of only one denier. The terminology "multi-denier" refers to a fabric formed from a blend of two or more sets of fibers each set of fibers having a different denier value than the other set.

The present invention provides a favorable relation between the number of fibers per volume of a nonwoven fabric and the feeling of the pleasant touch obtained, while maintaining its fluid absorbency performance. A larger number of fiber ends in a nonwoven fabric which contact a wearer of the fabric results in a greater feeling of softness. For a given nonwoven fabric produced by "n" quantity of staple fibers which have a length "x" is perceived by a wearer as being more pleasant to the touch than a nonwoven fabric produced by "n/2" quantity of staple fibers which have a length "2x". The invention finds an optimized balance between the fluid handling performance of a nonwoven fabric (for example, velocity of transmission of liquid in one direction, and the quantity of liquid returned in the opposite direction, capacity of masking, softness, flexibility, etc.) and the quantity of the number of fiber ends available to provide a pleasant touch.

In a preferred embodiment, the fibers of the present invention have lengths between 10 and 80 mm, each length being different at least 2 mm from the other. Preferably, the fibers have lengths between 15 and 40 mm, each length differing at least 2 mm and preferably by at least 4 mm from the other.

In another preferred embodiment, the mixture of fibers of the present invention comprises between 2 and 15 different lengths, and more preferably between 2 and 6 different lengths.

In another preferred embodiment, in each set of fibers from 50% to 99% of the fibers are within 1% of the average fiber length of the set with the balance of fibers in the set being within 20% of the average fiber length of the mixture. Thus, if the average fiber length for a given set of fibers is 10 mm, then from 50% to 99% of the fibers in the set are within 1% of this length, the balance of fibers in the set being within 20% of this length. In a most preferred embodiment, from 80% to 90% of the fibers in the set are within 1% of the average fiber length, the balance of fibers in the set being within 10% of this length.

In another preferred embodiment, the nonwoven fabric is formed by a mixture of fibers having more than one denier, and more preferably, each set of staple fibers of specific length comprises at least two different denier, the values of which are preferably 2 and 5.

With reference to the denier of the fibers of the invention, fibers having a denier between 1 and 10 are suitable, preferably between 2 and 6. For one and same length of fiber, it is an advantage that between one and another different denier there might be a difference of at least one denier, preferably two denier. In an advantageous manner, all fibers having a single denier represent from 10% to 90% of the total amount of fibers of the mixture of fibers of the invention, preferably between more or less 30 to more or less 70%.

The nonwoven fabrics of the present invention preferably have a basis weight between 25 grams to 50 gsm, preferably in a range of from 30 gsm to 35 gsm and is most preferably 35 grams per square meter. The nonwoven fabrics of the present invention preferably have an apparent thickness between 0.15 and 0.40 mm. An additional benefit provided by the nonwoven fabric of the invention is that, for a given basis weight, the thickness of the fabric obtained from a mixture of multi-length fibers and multi-denier fibers is greater than that of a fabric formed with mono-length fibers and mono-denier, or of a fabric formed with single length fibers and multi-denier fibers, or of the product with multi-length fibers and mono-denier fibers. Such fabrics further provide the feeling of comfort and pleasant touch.

The utilization of multi-denier, multi-length fibers perceptibly further increases the feeling of a pleasant touch. Further in accordance with the present invention, a new absorbent article is provided with a permeable covering for contact with the user's body, comprising a nonwoven fabric formed by a network of interconnected multi-length thermoplastic fibers, and the fibers possess a mixture or combination of at least two different lengths varying between 2 and 100 mm, and including a difference of at least 2 mm between themselves.

Further in accordance with the present invention, a new feminine sanitary napkin is provided with a liquid permeable body-facing cover, a liquid impermeable garment-facing lining, and an absorbent core between the liquid permeable covering and the liquid impermeable lining, wherein the liquid permeable covering comprises a nonwoven fabric formed by a network of interconnected multi-length staple fibers, wherein the fibers possess a combination of at least two different lengths, varying between 2 and 100 mm, and comprising a difference between the two lengths of at least 2 mm.

The absorbent articles of the present invention absorb body fluids and they are useful as disposable items such as, for example, diapers, feminine sanitary napkin, tampons, swaddling clothes, surgical bandages and cleansing fabrics. They may be used as separate articles or as necessary parts of disposable belongings or for limited use.

Suitable fibers for use in the present invention include, but are not limited to any conventional staple synthetic fibers such as polymeric fibers including polypropylene, acetate, rayon, dynel, nylon, acrylic, Orlon, Dacron, Vicara, polyester, polyethylene, polyacrylate and mixtures thereof, and are preferably polypropylene fibers.

Further in accordance with the present invention is the utilization of bi-component fibers ("core-shell"), where the polymer of the core of the fiber is different from the polymer of the external layer of the fiber. Further in accordance with the present invention are the cross-section fibers which are different from the circular ones, for example, bilobal fibers, trilobal fibers, etc.

The capacity for masking absorbed fluids by a nonwoven fabric, chiefly with reference to menstruation, is an important consideration in the development of covering materials for feminine sanitary napkin. It is much appreciated if such a covering has the ability of permitting a quick flow of the menstrual fluid towards the absorbent material, thus preventing the clear vivid sight of the fluid that has just been absorbed. Therefore, the fibers of the nonwoven fabric of the present invention are preferably provided with pigment material, preferably white colored, such as for example, titanium dioxide, calcium carbonate, and mixtures thereof. Titanium dioxide is the preferred pigment material. The quantity of the pigment material in the fibers must be sufficient to provide the fibers with opacity, thus providing the nonwoven fabric with an enhanced ability to mask the absorbed fluids. The amount of titanium dioxide in the fibers is between 1 and 6 percent in weight and is preferably between 2 and 3.5 percent in weight.

When the nonwoven fabric of the invention is used as a covering for a disposable absorbent article for contact with the user's body, it is usually desirable that such covering have a durable hydrophilic finish so that the portion of the disposable absorbent article which is in contact with the user's body remains hydrophilic after multiple introductions or passages of liquid. Hydrophilic finishes provide a better transportation of body fluid away from the user, and the body fluids are more efficiently taken towards the nearby absorbent core resulting in a cleaner, dryer feeling to the user. The fibers of the present invention may provided with a durable hydrophilic finish by treating the fibers with a surface active agent, such as, for example, a non-ionic surface active agent which is commercially available from ICI Polymer Additives, New Castle, Del., under the name "ATMER". Other adequate surface active agents, without excluding any other, are sodium salts of dioctylsulphosuccinate (commercially available from American Cyanamid under the name AEROSOL OT), monolaurate of non-ionic polyoxyethylene sorbitate (commercially available from ICI Polymer Additives, New Castle, Del. under the name TWEEN 20), and similar products. The durable hydrophilic finish may be applied to the surface of fibers by immersing them in an aqueous solution of the desired surface active agent, or by spraying an aqueous solution of the desired surface active agent on the surface of the fibers and drying them subsequently. Alternatively, the surface active agent may be applied to the nonwoven fabric with the help of a cylinder which is previously wetted by an aqueous solution of the desired surface active agent for contacting the internal surface of the nonwoven fabric so that the opposite external surface might retain its original hydrophobic characteristic. Alternatively, internal hydrophilic surfactant active agents or wetting agents may be directly incorporated into the thermoplastic polymer during the manufacture of fibers. Suitable wetting agents include, but are not limited to, nonionic surfactants based on ethylene oxide/fatty alcohol ether, ethoxylates of propylene oxide with propylene glycol, fatty esters of sorbitol and glycerol, and other similar products. Any other agents and additives known to the expert which endow fibers, and consequently nonwoven fabrics as well, with specific properties may be used without interfering in the purpose of the invention.

The nonwoven fabrics of the present invention may be formed by conventional processes including "thermobonding", "resin bonding" and "spunlacing". In all those manufacturing processes, the initial step is to form a veil of homogeneously mixed fibers. Generally, bundles of fiber sets, each set having different lengths, are mixed in an air mixing chamber and, subsequently, the fibers are either combed to form a combed veil or randomly placed on a perforated conveyor in order to form a continuous veil. When the thermal sealing process is used ("thermobonding"), the veil of fibers homogeneously mixed may be fed to a calendering station equipped with a heated smooth roller and a roller with relief standard that link the fibers and stabilizes the veil into a nonwoven fabric.

In a chemical sealing process ("resin bonding"), the veil of homogeneously mixed fibers is formed as described above and taken through a molding cylinder equipped with a series of water spray nozzles (for example, with a pressure around 200 psi), capable of causing a slight entanglement of the fibers. Then water is removed from the veil of entangled fibers by feeding it to a station where it is impregnated with a bonding material, being subsequently dried and hardened in a thermal transference equipment. Alternatively, the fiber veil may be submitted to powder resin spray, under vacuum and subsequently dried and hardened under forced air passage.

Finally, in a "spunlace" process, the homogeneous mixture of fibers of different lengths passes through a series of high pressure water jets, for example, from 500 to 1500 psi, so as to deeply entangle the fibers of the veil until a stabilized fabric is obtained. Then the water contained in the fabric is removed, and the fabric is dried.

All the processes mentioned herein are well known to the expert and the choice of one or other process is not, per se critical to the invention, provided of course that the resulting nonwoven fabrics possess sufficient structural integrity so that the fabric is suitable for use as a covering material for absorbent articles. In general, a nonwoven fabric has sufficient structural integrity for use as a covering material for absorbent articles when the tensile strength reaches about one pound per inch. Sufficient structural integrity is generally obtained when the sealing area comprises between 10 and 40% of the total superficial area of the fabric, and the sealing area is preferably between 15 to 20% of the total superficial area of the fabric. It is preferable that the nonwoven fabric of the invention be a carded or combed mantle by the "thermobonding" process for hot sealing by making use of heated roll calender with relief standard.

As is well known, absorbent articles which are externally used such as feminine sanitary napkins generally comprise a liquid impermeable garment-facing lining, a liquid absorbent core which is a layer of fiber absorbent material positioned on the lining, and a liquid permeable body-facing covering. Conventional covering materials include nonwoven fabrics formed by a network of oriented and interconnected fibers.

In accordance with the present invention, a novel feminine sanitary absorbent article has been provided with a liquid permeable covering which is turned towards the user's body, a liquid impermeable lining which is in opposite direction to the permeable covering and turned towards the user's clothes, and an absorbent core between the permeable covering and the impermeable lining, characterized in that the permeable covering comprises a nonwoven fabric formed by a network of interconnected multi-length staple fibers, preferably thermoplastic fibers, the fibers further comprising a mixture of at least two different sets of fibers, each set of fibers having different average lengths varying from 2 to 100 mm, and with a difference between the average fiber length of each set of at least 2 mm. The liquid permeable covering and the liquid impermeable lining are substantially co-extensive and are attached to each other along the periphery of the absorbent article through thermal fusion, adhesion, or any other convenient manner. The absorbent core is preferably adhesively attached to the impermeable lining by one or more glue lines.

The liquid impermeable lining is on a garment-facing side of the absorbent article and may be made of any flexible material which is capable of preventing the flow of fluid therethrough. Suitable materials include polypropylene films, polyethylene films, polyester films, polyamide films, vinyl polyethylene-acetate films, polyvinyl chloride films, and polyvinylidene films. Laminated and co-extruded combinations of the films mentioned may also be used, when such combinations are possible, by taking into consideration the physical and chemical properties thereof. Non-reticulated films which are impermeable to fluids and papers lined with hydrophobic materials may also be used. Films which are barriers against fluids, though permitting the flow of gases, called "breathable films, may also be used such as, for example, polyurethane films and microporous films, where the microporosity is created by ionizing radiation or by leaching out soluble inclusions using aqueous or non-aqueous solvents. Fabrics having fluid repellant surfaces or having small pores due to the packing of fibers, or when the pore diameters have been reduced, may also be used, both individually and together with breathable films, or breathable barriers. A particularly preferred barrier film is an opaque film of polyolefin, such as, for example, polyethylene which is impermeable against body fluids and which is about 20 microns thick. Polyester is another suitable lining material, such as for example, polyethylene terephthalate having a thickness of about 4 microns.

The absorbent core may be a mass of defiberized pulp fibers having a relatively high absorption capacity. The absorbent core usually is rectangle shaped and it occasionally has lateral edges which are curved inwardly as in the form of an hour glass. The absorbent core is slightly smaller than the lining sheet and smaller than the nonwoven covering. The absorbent core also may be a fiber panel with a densified integral layer. In this embodiment, it is preferred that the absorbent core be positioned on the lining sheet of the absorbent article so that the densified layer might be attached to the lining. The densified layer has the capacity for absorbing and retaining the liquid which is relatively higher than the rest of the panel previously mentioned and it is usually formed by a slight moistening of one surface of the panel, and subsequently compressing the moistened surface. The absorbent article may optionally comprise an absorbent structure with multi-layers, which may possess, in addition to the absorbent core, a transfer layer, which is a low density layer for acceptance and distribution of fluid, usually located between the absorbent core and the covering sheet. The transfer layer may comprise materials and structures which are relatively less hydrophilic than the contents of the absorbent core, such as "meltblown" veils of polyester of polypropylene fibers. Such veils may further contain wood pulp within themselves. Transfer layers also may contain nonwoven veils of low density and high softness comprising wood fibers and synthetic fibers such as polyethylene, polypropylene, polyester, polyacrylonitrile and polyamide. Such soft veils may be stabilized with chemical adhesives by thermal means such as "through air bonding".

The thickness of the absorbent structure may be uniform along its whole surface, according to the requirements of specific conformability, flexibility and absorption, or alternatively it may be thicker in certain parts. For example, a profile of thickness particularly preferable is an absorbent structure which is thicker in the central part than in its peripheral parts.

The fluid-impermeable barrier lining facing the user's clothes may be stabilized or otherwise adhered to the surface of the absorbent structure, in all its length or in discrete sealing zones. The barrier lining which is turned towards the user's clothes may be attached to the covering sheet in a super imposing configuration, for example, parallel to the sides of the absorbent structure, parallel to the bottom of the absorbent structure, or peripherally sealed by lateral extensions to the absorbent structure.

EXAMPLE

A practical example for carrying out a preferred alternative of the invention is given below, the only purpose of which is to illustrate and to give details about it, without creating any limitations, because other possible variations are presented to the expert about the subject, without impairing the purpose and the meaning of the invention.

Four types of nonwoven fabrics manufactured by the "thermobonding" process were evaluated, herein named A, B, C and D and their compared properties. The raw material was polypropylene homopolymer, containing 2.5% in weight of glittering titanium dioxide inserted during the fabrication of the fiber, and the density of fabrics was 35 g/m2.

Table 1 below shows the distribution of the quantity of fibers per cm2 for each of the fabrics used in the test (numbers between brackets show the denier of the corresponding fiber).

TABLE 1

NUMBER OF FIBERS PER SQUARE CENTIMETER

| Length of Fiber (mm) | Type of Nonwoven Fabric | | | |
|---|---|---|---|---|
| | A | B | C | D |
| 16 | 66 (3d) 66 (5d) | — | — | — |
| 20 | 34 (3d) 34 (5d) | — | — | — |
| 32 | 49 (3d) 49 (5d) | — | — | — |
| 40 | 16 (3d) 16 (5d) | 98 (3d) 98 (5d) | 393 (2d) | 157 (5d) |
| Total/cm² | 330 | 196 | 393 | 157 |

Note: The calculation for the number of fibers per square centimeter was determined by the formula:
x = 0.9 g/d c, where:
x = number of fibers per square centimeter
g = basis weight (grams per square meter)
d = denier (grams/9000 meters) - (Note: value is averaged if there is more than one denier present)
c = length of fiber (meters)

EXPLANATION FOR THE COMPARISON

Fabric A corresponds to a preferred performance of the invention, nonwoven multi-denier and multi-length fabric. Fabric B corresponds to a nonwoven multi-denier mono-length fabric. Fabric C is the reference fabric regarding the softness, comprising uniform length fibers of denier 2, while fabric D is the reference fabric regarding the low retention of liquid, comprising uniform length fibers of denier 5.

Fabrics C and D demonstrate the difficulty of obtaining a nonwoven fabric of balanced properties. On one hand, the softest fabric commonly used in commercial products is fabric C, with a few disadvantages, for example, high retention of liquid. Fabric D, on the other hand, formed from larger denier fibers, eliminates the problem of high retention of liquid, but it is very rough.

Table 2 below shows the results of various evaluations referring to fabrics A, B, C and D. The values expressed in each column indicate the relative performance among the four products tested by giving mark 1 to the worst performance and mark 4 to the best performance.

TABLE 2

PERFORMANCE MARKS
Parameter Type of Nonwoven Fabric

| | | A | B | C | D |
|---|---|---|---|---|---|
| 1. | Retention of liquid | 2 | 3 | 1 | 4 |
| 2. | Fitting | 3 | 2 | 4 | 1 |
| 3. | Number of ends/cm² | 3 | 2 | 4 | 1 |
| 4. | Return of liquid | 2 | 3 | 1 | 3 |
| 5. | Apparent thickness | 4 | 3 | 1 | 2 |
| 6. | Softness | 3 | 2 | 4 | 1 |
| Average of six parameters | | 2.8 | 2.5 | 2.5 | 2.0 |

CONCEPT OF PARAMETERS EVALUATED

The concepts evaluated shall be explained by taking the example of a feminine sanitary napkin in which the nonwoven fabric, according to the invention, is the covering, namely, the material for contact with the user's body.

1. Retention of liquid

This measure refers to the quantity of liquid retained in the fabric after going through it. The greater the retention of liquid (lowest mark) the greater the feeling of humidity transmitted to the user's body. It is, therefore, a partial measure of the comfort propitiated by the contact with the user's body.

2. Fitting

This measure refers to the conformability or adaptation of the fabric to the user's body. For example, a "soft" fabric fits better to the body (highest mark) than a "hard" fabric. Additionally, the "hard" fabric is rougher than the "soft" fabric. This is another partial measure of the comfort offered to the user.

3. Quantity of fibers ends per $cm^2$.

This measure refers to the feeling of pleasant touch caused by the contact of the ends of the fibers of the fabric on the skin, as previously explained. The larger the number of ends (highest mark) the more pleasant the feeling. This is another partial measure of the comfort offered to the user.

4. Return of liquid

This measure refers to the quantity of liquid which returns to the nonwoven fabric after going through the nonwoven fabric, lining the adjacent absorbent body. The smaller the return of liquid (highest mark) the smaller the feeling of humidity transmitted to the user, and, among other things, making the user sure that the product will not be leaking. This refers to another partial measure of the comfort offered to the user.

5. Thickness

Firstly, this measure refers to a "paper or cardboard" feeling that may occur for a certain relation between density/thickness. The greater the thickness (highest mark) the less of a "paper or cardboard" feeling transmitted to the user.

Secondly, it also refers to the visual perception of being apart from the fluid absorbed by the adjacent absorbent core and the surface for contact with the body. That is to say, for the same quantity of titanium dioxide, the greater the thickness (highest mark) the more distant the absorbed blood seems to be from the surface. This is another partial measure of the comfort offered to the user.

6. Softness

Softness refers to a measure for the feeling of pleasure to the touch in a general way, without mentioning any other property of the product which is more specific. It is that feeling transmitted by handling a piece of nonwoven fabric. The better the feeling (highest mark) the pleasanter is the product. It is also a partial measure of the comfort offered to the user.

ANALYSIS OF THE RESULTS OBTAINED

Nonwoven fabric A of the invention provided superior performance in all parameters evaluated and this fact makes it a superior product when compared with the conventional existing nonwoven fabrics because it does not have any disadvantage that could be harmful to its use.

Fabric C.—regarded here as the reference relating to softness,—is the worst one among the four types evaluated with reference to the retaining of liquid, return of liquid and apparent thickness.

Fabric D,—regarded here as the reference relating to the low retaining of liquid,—is the worst one among the four types evaluated with reference to its fitting, number of ends and softness.

Fabric B,—though comprising the same graduation scale of fabric C,—is successful in reducing the deficiencies of the latter and of fabric D, but the results thereof are still inferior to those of the nonwoven fabric of the invention.

In summary, the average of values of non-woven fabric A of the invention,—obtained from the evaluation of sundry properties,—was the highest one among the four nonwoven-fabrics. Additionally, no parameter has indicated an entirely unfavorable performance (mark 1) in relation to the other ones.

ANALYTICAL METHODS

1. RETENTION OF LIQUID

Principle of the method: a quantity of synthetic menstrual fluid is placed on a specific area on the surface of a pre-weighed nonwoven fabric, which rests on a block of absorbent material. After the flow of the fluid, the nonwoven fabric is removed and weighed—The difference between the final weight and the initial weight of the nonwoven fabric is considered as the retaining of liquid.

Analytical Method Data:

synthetic menstrual fluid—formulation described in patent application WO1510996, page 37;

quantity of synthetic menstrual fluid—7 ml;

—specific area on the surface the nonwoven fabric: oval hole (3.9 by 2.5 cm) of an acrylic plate measuring 27 cm by 11 cm by 7.5 cm, (weight 276.4 g), which rests on a nonwoven fabric during the test;

block of absorbent material: bleached pulp of long wood fibers, dimensions: 210 by 55 by 12 mm, density: 0.06 g/cm3.

pouring out of synthetic menstrual fluid: quickly, in one stroke.

time elapsed between the beginning of pouring out of synthetic menstrual fluid and weighing of nonwoven fabric: 2 minutes.

2. FITTING—standard test INDA IST 90.3–92 (INDA)= "Association of the Nonwoven Fabrics Industry, United States of America).

3. NUMBER OF ENDS—theoretically provided by double the number of fibers/cm$^2$. In practice, a small quantity of ends may not be available because they are obstructed in the thermobonded areas.

4. RETURN OF LIQUID

Principle of the method: a quantity of synthetic menstrual fluid is placed on a specific area on the surface of a pre-weighed nonwoven fabrics which rests on a block of absorbent material. The wetted area is covered by an absorbent sponge, previously weighed, and placed under a specific pressure during a certain period of time. The fluid mass removed from the block of absorbent material by the absorbent sponge is considered as the return of liquid.

The analytical method data are the same used in the method for the RETENTION OF LIQUID including:

absorbent sponge: Extra Absorbent Bandage measuring 7.5 cm×7.5 cm manufactured by Johnson & Johnson Industrial e Commercio, Brazil.

Use of pressure—5 minutes after the whole fluid has passed through the block of absorbent material, the same is placed on a hard and flat surface. Two sponges, which are folded four times, are placed on the wetted spot. A standard weight of 2.2 kg, and dimensions: 5.1 by 10.2 by 5.4 cm, is placed on the sponges (resting on the surface measuring 5.1 cm by 10.2 cm) producing a pressure of approximately 4.14 kPa. The weight is removed after 3 minutes as well as the sponges which are immediately weighed. The difference of weight between the sponges before and after the absorption of synthetic menstrual fluid represents the return of liquid.

5. THICKNESS—Standard test INDA IST 120.1–92

6. SOFTNESS

Softness is a subjective measurement that is assigned to samples by relative comparison. A fabric was cut into squares of approximately 10 by 10 cm of each of the four nonwoven fabrics tested. The samples were freely handled and the "feeling" relating to softness among the samples was determined.

It is understood that the foregoing example refers only to performance illustrated as a specific example of the present invention, and is not to be construed as limiting the invention in any way except as provided in the appended claims attached hereto.

We claim:

1. An absorbent article comprising a liquid permeable body-facing cover layer, a liquid impermeable garment-facing barrier layer and an absorbent core between the cover layer and the barrier layer, the cover layer comprising a nonwoven fabric formed from a network of interconnected synthetic staple fibers, the fibers comprising a mixture of a first set of fibers and a second set of fibers, each set of fibers having an average length of from 2 mm to 100 mm, wherein the average length of the first set of fibers varies from the average length of the second set of fibers by at least 2 mm.

2. The absorbent article according to claim 1, wherein the fibers further comprise at least two different denier.

3. The absorbent article according to claim 1, wherein the fibers have lengths between 10 mm and 80 mm and the length of the first set of fibers is greater than the length of the second set of fibers by at least 4 mm.

4. The absorbent article according to claim 1, wherein the fibers have lengths between 15 mm and 40 mm and the length of the first set of fibers is greater than the length of the second set of fibers by at least 4 mm.

5. The absorbent article according to claim 1, wherein the nonwoven fabric has a basis weight between 25 g/m$^2$ and 35 g/m$^2$.

6. The absorbent article according to claim 1, wherein the nonwoven fabric has an apparent thickness between 0.15 mm and 0.40 mm.

7. The absorbent article according to claim 6, wherein the nonwoven fabric has a basis weight of 35 g/m$^2$.

8. The absorbent article according to claim 1, wherein the absorbent article is selected from the group consisting of sanitary napkins, panty liners, diapers and adult incontinence devices.

9. The absorbent article according to claim 1, wherein the mixture of fibers comprises between 2 and 10 sets of fibers and each set of fibers has a different length.

10. The absorbent article according to claim 1, wherein the mixture of fibers comprises between 2 and 6 sets of fibers and each set of fibers has a different length.

11. The absorbent article according to claim 1, wherein the fibers in the first set have a first denier and the fibers in the second set have a second denier and there is a difference of at least one denier between the fibers in first set and the fibers in the second set.

12. The absorbent article according to claim 1, wherein the fabric has an apparent thickness between 0.15 mm and 0.40 mm.

13. The absorbent article according to claim 1, wherein the fibers include a pigment material.

14. The absorbent article according to claim 13, wherein the pigment material is titanium dioxide in an amount from about 1% to 6% by weight.

15. The absorbent article according to claim 13, wherein the titanium dioxide is in an amount from about 2% to 3.5% by weight.

* * * * *